United States Patent [19]

Kilpatrick

[11] Patent Number: 4,918,057

[45] Date of Patent: Apr. 17, 1990

[54] VETERINARY PREPARATIONS

[75] Inventor: Michael J. Kilpatrick, Horton Cum Studley, United Kingdom

[73] Assignee: Glaxo Group Limited, London, United Kingdom

[21] Appl. No.: 68,446

[22] Filed: Jun. 30, 1987

[30] Foreign Application Priority Data

Jul. 1, 1986 [GB] United Kingdom ................. 8615995

[51] Int. Cl.$^4$ .............................. A61K 31/70
[52] U.S. Cl. ...................... 514/30; 424/442
[58] Field of Search ............. 514/30, 9, 129, 394, 514/445, 469, 533, 555, 648, 649, 653, 865; 424/442

[56]  References Cited

U.S. PATENT DOCUMENTS

| | | | |
|---|---|---|---|
| 4,382,958 | 5/1983 | Duckworth | 514/653 |
| 4,432,993 | 2/1984 | Ferris | 514/469 |
| 4,442,300 | 4/1984 | Olsson et al. | 514/533 |
| 4,478,849 | 10/1984 | Ainsworth et al. | 514/445 |
| 4,513,001 | 4/1985 | Joannie et al. | 514/394 |
| 4,537,879 | 8/1985 | Hamill et al. | 514/9 |
| 4,557,932 | 12/1985 | Tybring | 514/865 |
| 4,622,341 | 11/1986 | Szatlóczky et al. | 514/648 |
| 4,622,342 | 11/1986 | Cantello et al. | 514/653 |
| 4,654,371 | 3/1987 | Ainsworth et al. | 514/555 |
| 4,692,333 | 9/1987 | Pirali et al. | 435/129 |
| 4,751,071 | 6/1988 | Magruder et al. | 514/649 |

OTHER PUBLICATIONS

V. Aldrovandi et al., "First Observations in the Use of Salbutamol in Respiratory Diseases of Calves", & Obiettivi E. Documenti Veterinari, vol. 3, No. 9, 1982, p. 55.

A. Narita et al., "Effects of Antibiotics on the Actions of Antiasthmatic Agents in Guinea Pig Excised Trachea Muscle", & Showa Igakkai Zasshi, 1983, 43(5), pp. 569–583.

*Primary Examiner*—Ronald W. Griffin
*Assistant Examiner*—Pamela S. Webber
*Attorney, Agent, or Firm*—Morgan & Finnegan

[57] ABSTRACT

A method for improving the growth rate, feed conversion efficiency and/or the ratio of carcass lean to carcass fat of domestic animals comprising the administration to said animals of salbutamol or an acid addition salt thereof in combination with an antimicrobial agent.

20 Claims, No Drawings

VETERINARY PREPARATIONS

This invention relates to veterinary preparations and to their use as growth promoters in domestic livestock such as pigs, sheep, cattle and poultry. More specifically, the veterinary preparations according to the invention comprise the β-adrenergic stimulant, salbutamol or an acid addition salt thereof, in combination with certain antimicrobial agents. The invention also relates to methods for improving feed conversion efficiency with reduction in carcass fat and increase in carcass lean and improving live weight gain in such animals.

Because of the present requirements of the consumer, it is desirable to produce leaner domestic livestock with a high ratio of carcass lean to carcass fat. Thus, by increasing lean content and decreasing the fat content, the carcasses of the animals grade to a higher standard at slaughter.

It is particularly desirable to increase the lean content and decrease the subcutaneous fat in pigs, particularly those pigs prone to higher fat deposition. It is important, however to maintain the quality of the tissues and the organoleptic qualities of the carcasses after slaughter.

European patent application 146738 describes the use of animal feed compositions comprising certain 1-(aminophenyl)-2-ethanols in conbination with antimicrobial agents. However, this would not indicate or suggest that veterinary preparations containing salbutamol or an acid addition salt thereof in combination with an antimicrobial agent would have an optimal effect on live weight gain in domestic livestock and which would improve their feed conversion efficiency with reduction in carcass fat and increase in carcass lean greater than would be anticipated from effects attributable to salbutamol or an acid addition salt thereof when used alone. The patent specification referred to above does not also disclose the compatibility which exists between salbutamol or an acid addition salt thereof and certain antimicrobial agents. Moreover, the β-adrenergic stimulants described in the patent specification give rise to significant undesirable cardiovascular side-effects such as increased heart rate when administered to sheep and calves and pronounced appetite suppression in sheep (The Veterinary Record, Apr. 18, 1987, pages 381-383); there is clearly a need for improved feed compositions which avoid this problem.

Thus, we have surprisingly found that, by administering salbutamol or an acid addition salt thereof together with at least one antimicrobial agent, it is possible to improve feed conversion efficiency, live weight gain in domestic livestock and increase the carcass lean content.

According to the present invention therefore we provide a method for improving the growth rate, feed conversion efficiency and/or the ratio of carcass lean to carcass fat of domestic livestock comprising the administration to said animals of salbutamol or an acid addition salt thereof in combination with an antimicrobial agent.

Acid addition salts of salbutamol include salts with organic and inorganic acids. The preferred form of salbutamol for use in the method of the invention is salbutamol sulphate.

The antimicrobials useful in the present invention include growth promoting or therapeutic antimicrobials. The growth promoting antimicrobials are preferred. Examples of such antimicrobials are macrolides, for instance tylosin and spiramycin; peptides such as bacitracin and avoparcin; lipopolysaccharides such as bambermycin; peptolides such as virginiamycin; quinioxalines such as olaquindox; and nitrofurans such as nitrovin. Tylosin, virginiamycin, bacitracin and avoparcin are particularly preferred. Therapeutic antimicrobials which can be used are for example, chlortetracycline, sulphadimidine, furazolidone, tiamulin, dimetridazole and penicillin. Tiamulin is the preferred therapeutic antimicrobial for use in pigs. A combination of a growth promoting and therapeutic antimicrobial could also be used.

We have observed that the method of the invention is especially effective in non-ruminants, and, in particular, in pigs. The increase in the ratio of lean to fat content is particularly beneficial in the case of pigs prone to high fat deposition such as castrates and gilts and pigs which genetically lay down more fat, such as the Yorkshire, Duroc, Hampshire, Camborough blue and Saddleback breeds and crossbreeds from these.

The salbutamol compound is preferably administered in the range 5 to 400 micrograms/kg live weight per day. In general, it is preferred that the daily intake of salbutamol should be above 30 micrograms/kg live weight; more preferably above 40 micrograms/kg, especially where pigs are concerned. A preferred upper daily intake limit is 250 micrograms/kg. Optimal levels vary somewhat from species to species but can readily be determined.

The antimicrobial is preferably administered in the range of 0.06 to 14 mg/kg live weight per day (2-400 ppm in the diet at 2-2.5 kg/pig/80 kg live weight) to 0.15-1.2 mg/kg live weight per day (5-40 ppm).

The salbutamol compound is preferably given orally in combination with the antimicrobial agent. The salbutamol and antimicrobial agent may conveniently be administered in admixture with the feed. In the case of pigs, the feed is advantageously administered over a period of at least 60 days and the animals may be fed ad libitum, to appetite or restricted to below normal appetite.

The preferred concentration of salbutamol or salt thereof in the feed, for daily ingestion of the drug, is 2 to 12 parts per million (ppm), preferably 2-4 ppm and more preferably 3 ppm.

The preferred concentration of the antimicrobial in the feed, for daily ingestion of the drug, is 2-1000 ppm preferably 2-500 ppm and more preferably 2-400 ppm. However, it is anticipated that for maximum effect the antimicrobials are administered in the ranges defined below:

| Antimicrobial | Broad Range | Preferred Range |
| --- | --- | --- |
| Tylosin | 5-50 ppm | 10-40 ppm |
| Virginiamycin | 10-100 ppm | 20-50 ppm |
| Bacitracin | 2-100 ppm | 5-50 ppm |
| Avoparcin | 2-100 ppm | 5-40 ppm |
| Spiramycin | 1-60 ppm | 5-50 ppm |
| Bambermycin | 1-20 ppm | 2-6 ppm |
| Olaquindox | 10-200 ppm | 25-100 ppm |
| Nitrovin | 5-50 ppm | 5-15 ppm |
| Chlortetracycline | 100-500 ppm | 200-450 ppm |
| Sulphadimidine | 50-200 ppm | 80-120 ppm |
| Furazolidone | 100-500 ppm | 200-300 ppm |
| Tiamulin | 10-200 ppm | 20-100 ppm |
| Penicillin | 50-500 ppm | 100-300 ppm |
| Dimetridazole | 100-1000 ppm | 200-500 ppm |

According to a further feature of the invention we provide an animal feed composition for improving the growth rate and feed conversion efficiency of domestic livestock said composition containing 2 to 12 parts per million of salbutamol or an acid addition salt thereof and 2-1000 parts per million of an antimicrobial agent.

The concentration of salbutamol or salt thereof in the feed composition is more preferably less than 8 ppm, for example in the range 2-4 ppm, the most preferred range being 2-3 ppm.

The concentration of the antimicrobial agent in the feed composition is preferably 2-500 ppm and more preferably 2-400 ppm, the most preferred range is 2-100 ppm.

At the higher concentrations of salbutamol, the feed may be less palatable than the unmedicated feed. In this case, it may be beneficial to mask the flavour of the drug, for example by incorporation of flavouring agents or encapsulation of the drug in readily digestable material.

The animal feeds generally used are various mixtures of grain and high protein raw materials containing for example, barley or maize mixed with soya or fish meal or similar high protein materials. Alternatively, the animals may be fed on food by-products such as skim milk, whey or bakery offal.

The animal feed compositions are commonly prepared by admixing or incorporating a premix comprising salbutamol or an acid addition salt such as salbutamol sulphate with a sufficient amount of animal feed to provide the desired concentration of salbutamol compound in the feed. Alternatively, the premix may be first supplemented with a vitamin/mineral/amino acids mixture before incorporation into the animal feed. The antimicrobial agent could be incorporated into the premix or added to the animal feed at the desired concentration. It is preferred however, to add the antimicrobial agent direct to the feed.

For commercial purposes, the premix may contain the active ingredients mixed in a high concentration with a carrier material which is usually a desirable inclusion in the complete feed such as wheat flour, soya bean meal, corn oil, ground maize, barley, mineral mixtures such as vermiculite or diatomaceous earth, corn gluten meal, corn distillers solubles, soya flour, calcium sulphate, limestone flour or calcium carbonate. The premixes may for example, have a concentration of 0.01% to 2.0% by weight of salbutamol with a preferred concentration of 0.4%-1% by weight. If an antimicrobial agent is to be incorporated, the premix will have a concentration of 1.0% to 10.0% by weight of the antimicrobial agent with a preferred concentration of 2.0% to 6.0% by weight.

The premix or the supplemented premix may be mixed with the complete animal feed, spread over the animal feed or dissolved in water. Preferably, the premix is supplied as a concentrate which contains 0.40% w/w of salbutamol sulphate blended with wheat flour up to 100.00% w/w. The dry blend is agglomerated with water and dried and the product is then sieved and packed.

The preferred medicated feed for animals for example poultry, pigs, cattle and sheep would usually contain from 2 g to 8 g of salbutamol per tonne of feed, the optimum amount being about 2 g to 4 g preferably 2 g to 3 g per tonne of feed. If an antimicrobial agent is added the medicated feed would contain from 2 g to 500 g of the antimicrobial agent per tonne of feed.

The unmedicated feeds are generally available from animal feed suppliers. The names and addresses of some of the suppliers in the UK are given below:

| Name of Animal Feed Suppliers | Address |
| --- | --- |
| Dalgety Agriculture Ltd | Dalgety House |
| | The Promenade |
| | Clifton |
| | Bristol |
| | BS8 3NJ |
| BOCM - Silcock Ltd | Basing View |
| | Basingstoke |
| | Hants |
| | RG21 2EQ |
| J. Bibby Agriculture Ltd | Adderbury |
| | Banbury |
| | Oxon |
| | OX17 3HL |

EXAMPLE 1

Premix Composition

| Ingredient | % By Weight | Quantities for a Batch Size of 500 Kg |
| --- | --- | --- |
| Salbutamol Sulphate | 0.40 | 2.00 Kg |
| Tylosin Phosphate | 5.30 | 26.50 Kg |
| Wheat Flour | to 100.00 | 471.50 Kg |

The premix composition in Example 1 would be mixed thoroughly into the complete feed at a level of 0.75 kg per tonne of feed to give 3 ppm of salbutamol sulphate and 40 ppm tylosin phosphate and fed to pigs continously from approximately 6-10 kg live weight of pigs. This premix composition would be primarily used for pigs up to 4 months of age. For older pigs a premix composition containing a lesser amount of tylosin phosphate would be used in order that the final feed contained about 20 ppm of tylosin phosphate after mixing in the same amount of premix. Alternative premix compositions containing different antimicrobials could be envisaged. The premixes may for example have a concentration of 0.01% to 2.0% by weight of the salbutamol sulphate with a preferred concentration of 0.4%-1.0% by weight of salbutamol sulphate.

EXAMPLE 2

Feed Composition

| Ingredient | % By Weight in final feed |
| --- | --- |
| Salbutamol Sulphate | 0.0003 |
| Tylosin Phosphate | 0.004 |
| Wheat | 59.69 |
| Barley | 20.00 |
| Soya Bean | 18.50 |
| Mineral/Vitamin Mixture | 1.18 |

EXAMPLE 3

Feed Composition

| Ingredient | % By Wheat in final feed |
| --- | --- |
| Wheat | 65.11 |
| Grimsdale fat | 2.17 |
| Hi protein soya | 25.00 |
| Limestone flour | 0.60 |
| Dical | 1.00 |

-continued

| | |
|---|---|
| Salt | 0.40 |
| Kaolin | 2.45 |
| Molasses | 3.00 |
| Premix (Vitamins & Minerals) | 0.25 |
| Salbutamol sulphate | 0.0002 |
| Avoparcin | 0.00125 |
| Calculated analysis | % |
| Oil | 3.50 |
| Protein | 20.50 |
| Fiber | 0.34 |
| Calcium | 0.54 |
| Phosphorus | 0.54 |
| Lysine | 1.03 |
| Available Lysine | 0.97 |
| Sodium | 0.17 |
| Lineoleic | 0.93 |

EXAMPLE 4

Conversion Efficiency by 2 ppm salbutamol in the absence of an antimicrobial agent Male, castrate and female pigs (pure bred Large White) in equal numbers were fed individually ad libitum on the diet set out below containing 0 and 2 ppm salbutamol sulphate (12 pigs per group). The pigs were fed the diets from approximately 20 kg body weight for 15 weeks.

The mean feed intake (in grams) per pig per day and the mean live weight gain (in grams) per pig per day were recorded at 5, 10 and 15 weeks.

The averages for each of these values in respect of the groups is set out below.

| Feed Concentration | Average feed intake (g per pig per day) | Average live weight gain (g per pig per day) | Feed Conversion Efficiency (FCE) (g feed/g live weight gain) |
|---|---|---|---|
| 0 ppm salbutamol sulphate (controls) | 2911 | 1000 | 2.91 |
| 2 ppm salbutamol sulphate | 2839 | 1023 | 2.78 |

% improvement in FCE is 4.5% $\frac{(2.91 - 2.78 \times 100)}{2.91}$

The basal diet in the above procedure was as follows:

| | Basal Diet | |
|---|---|---|
| Composition (% w/v) | Pig grower diet (<50 kg bodyweight) | Pig finisher diet (>50 kg bodyweight) |
| Barley | 40.51 | 40.51 |
| Wheat | 10.00 | 10.00 |
| Maize | 15.00 | 15.00 |
| Extracted soya bean meal | 14.50 | 11.50 |
| Provimi 55 fish meal | 3.50 | 2.50 |
| Weatings | 10.00 | 15.00 |
| Dicalcium phosphate | 0.44 | 0.44 |
| Limestone flour | 1.05 | 1.05 |
| Salt | 0.25 | 0.25 |
| Molasses | 2.50 | 2.50 |
| Fat premix (50%) | 2.00 | 1.00 |
| Mineral/vitamin supplement | 0.25 | 0.25 |
| Theoretical analysis (%) | | |
| Oil | 3.25 | 2.85 |
| Crude protein | 16.95 | 15.66 |
| Fiber | 4.48 | 4.61 |
| Total digestible nutrients | 71.81 | 70.93 |
| Digestible energy | 13.00 | 12.75 |

-continued

| | Basal Diet | |
|---|---|---|
| Composition (% w/v) | Pig grower diet (<50 kg bodyweight) | Pig finisher diet (>50 kg bodyweight) |
| (MJ/kg (approx.)) | | |
| Lysine | 0.89 | 0.77 |
| Methionine and cystine | 0.56 | 0.51 |
| Calcium | 0.87 | 0.81 |
| Phosphorous | 0.60 | 0.59 |
| Salt | 0.47 | 0.46 |

EXAMPLE 5

Feed Conversion Efficiency by 2 ppm salbutamol in the presence of avoparcin (antimicrobial agent)

Male, castrate and female pigs comprising a mixture of Large White pedigree and crossbreeds (Large White back crossed into Large White cross Landrace) in groups of 15 were fed to appetite twice a day using BOCMS 451 Elite Gold Plus Diet. The pigs were fed the diets from approximately 30 kg to 80-90 kg at slaughter. The feed conversion efficiency is set out below.

| Feed Concentration 20 ppm Avoparcin | Feed Conversion Efficiency (FCE) |
|---|---|
| 0 ppm salbutamol sulphate (controls) | 2.59 |
| 2 ppm salbutamol sulphate | 2.11 |

% improvement in FCE is 18.5% $\frac{(2.59 - 2.11 \times 100)}{2.59}$

EXAMPLE 6

Feed Composition

| Basal Diet (Diet 1) Constituents g/kg | |
|---|---|
| Ground Barley | 739.3 |
| Soyabean meal 44 | 175.3 |
| Whitefish meal | 65.0 |
| L-lysine hydrochloride | 2.0 |
| Vitamin-trace element mix* | 2.5 |
| Ground limestone | 7.5 |
| Dicalcium phosphate | 6.5 |
| Salt | 1.9 |
| Chemical Composition (as fed basis) | |
| Dry Matter (g/kg) | 862.6 |
| Digestible energy (MJ/kg) | 13.1 |
| Crude protein (g/kg) | 190.0 |
| Total lysine (g/kg) | 11.7 |
| Threonine (g/kg) | 7.4 |
| Methionine + cystine (g/kg) | 7.0 |
| Calcium (g/kg) | 10.6 |
| Phosphorus (g/kg) | 7.1 |
| Na (g/kg) | 2.0 |
| Vitamin B12 (g/kg) | 28.5 |

*Providing in each kg diet, 5000 i.u. Vitamin A, i.u. cholecalciferol, 2.5 mg · tocopherol acetate, 2 mg riboflavin, 5 mg DL-calcium pantothenate, 5 mg nicotinic acid, 6 g cyanocobalamin, 1 mg vitamin D (menaphthone), 125 mg Cu, 100 mg Zn, 40 mg Mn, 50 mg Fe, 0.5 mg Co, 2 mg I and 0.1 mg Se.

Medicated Feed Composition

Salbutamol sulphate was mixed with the basal diet at a concentration of 2 ppm (Diet 2).

Similar feed compositions were made up containing 12.5 ppm avoparcin (Diet 3) and 2 ppm salbutamol sulphate+12.5 ppm avoparcin (Diet 4).

EXAMPLE 7

60 Camborough blue hybrid boars in equal number were fed ad libitum the following diets from Example 6:
Diet 1: Unmedicated (Basal diet of Example 6)
Diet 2: Basal diet+2 ppm salbutamol sulphate
Diet 3: Basal diet+12.5 ppm avoparcin
Diet 4: Basal diet+2 ppm salbutamol sulphate+12.5 ppm avoparcin The pigs were grown from an average weight of 26 kg to an average slaughter weight of 85 to 95 kg for 9 weeks.

The pigs were slaughtered and the depth of skin and fat at the $P_2$ position of the mid back was measured. In addition the right side of 8 carcasses from each treatment group were dissected using the butchery method (Brown and Wood, 1979, Pig Carcass Evaluation-Measurement of Composition using a Standardised Butchery method M.R.I. memorandum No. 42.) into the amount of subcutaneous fat, muscle, intermuscular fat bone and skin.

The results are set out below.

| Feed | Depth of back fat ($P_2$) (mm) | Feed Conversion Efficiency | % improvement in FCE |
|---|---|---|---|
| Diet 1 | 15.8 | 2.55 | |
| Diet 2 | 14.1 | 2.48 | 2.7% $\frac{(2.55 - 2.48 \times 100)}{2.55}$ |
| Diet 3 | 14.9 | 2.63 | |
| Diet 4 | 13.6 | 2.50 | 4.9% $\frac{(2.63 - 2.50 \times 100)}{2.63}$ |

EXAMPLE 8

The experiment in Example 7 was further extended and the weight of the muscle psoas major measured. The effect of inclusion of 2 ppm of salbutamol, 12.5 ppm avoparcin, and the 2 ppm salbutamol and 12.5 ppm avoparcin combined is shown in Table 1:

TABLE 1

The effect of inclusion of 2 ppm salbutamol and 12.5 ppm Avoparcin alone and combined upon carcass weight, lean and fat content mean ± SEM of Camborough blue boars

| | Treatment | | | |
|---|---|---|---|---|
| | Control | Salbutamol | Avoparcin | Salbutamol + Avoparcin |
| Carcass weight (kg) | 65.0 ± 3.1 | 67.2 ± 4.8 | 67.0 ± 3.4 | 66.7 ± 4.8 |
| Depth of backfat at last rib | 15.8 ± 3.4 | 14.1 ± 1.5 (−10.8%) | 14.9 ± 2.1 (−5.7%) | 13.6 ± 1.8 (−13.9%) |
| Weight of m. psoas major (Kg) | 3.9 ± 0.4 | 4.3 ± 0.4 (+10.3%) | 4.1 ± 0.3 (+5.1%) | 4.4 ± 0.3 (+12.8%) |

What is claimed:

1. A method for using veterinary preparations in domestic animals comprising the administration to said animals of salbutamol or an acid addition salt thereof in combination with an antimicrobial agent, thereby improving the growth rate, feed conversion efficiency or ratio of carcass lean to carcass fat of domestic animals.

2. A method as claimed in claim 1 in which salbutamol sulphate is used.

3. A method as claimed in claim 1 wherein the antimicrobial agent is selected from tylosin, virginiamycin, bacitracin, avoparcin and tiamulin.

4. A method as claimed in claim 1 in which the domestic animals are other than ruminants.

5. A method as claimed in claim 4 in which the domestic animals are pigs.

6. A method as claimed in claim 5 in which the pigs are of breeds which are prone to high fat deposition.

7. A method as claimed in claim 5 in which the pigs are gilts or castrates.

8. A method as claimed in claim 1 in which the salbutamol or an acid addition salt thereof is administered in the daily intake range 5-400 micrograms per kilogram live weight.

9. A method as claimed in claim 8 in which the salbutamol or an acid addition salt thereof is administered in the daily intake range 30-250 micrograms per kilogram live weight.

10. A method as claimed in claim 1 wherein the antimicrobial agent is administered in the daily intake range 0.06 to 14 milligrams per kilogram live weight.

11. A method as claimed in claim 10 wherein the antimicrobial agent is administered in the daily intake range 0.15 to 1.2 milligrams per kilogram live weight.

12. A method as claimed in claim 1 in which the salbutamol or acid addition salt thereof is administered to the animal orally in combination with the antimicrobial agent.

13. A method as claimed in claim 12 in which the salbutamol or acid addition salt thereof and the antimicrobial agent are administered to the animal in admixture with the feedstuff of the animal.

14. A method as claimed in claim 13 in which the concentration of salbutamol or acid addition salt thereof in the feedstuff is in the range 2-12 parts per million and the concentration of the antimicrobial agent is in the range 2-1000 parts per million.

15. A method as claimed in claim 14 in which the concentration of salbutamol or acid addition salt thereof in the feedstuff is in the range 2-4 parts per million and the concentration of the antimicrobial agent is in the range 2-400 parts per million.

16. A method for using veterinary preparations in pigs comprising the administration to said pigs of salbutamol or an acid addition salt thereof by the oral route at a daily intake greater than 30 micrograms per kilogram in combination with an antimicrobial agent, thereby increasing the growth rate, feed conversion efficiency or ratio of carcass lean to carcass fat of pigs.

17. An animal feed composition for improving the growth rate and feed conversion efficiency of domestic animals said composition containing 2-12 parts per million of salbutamol or an acid addition salt thereof and 2-1000 parts per million of an antimicrobial agent.

18. A composition as claimed in claim 17 in which salbutamol or an acid addition salt thereof is present in the concentration range 2-4 parts per million and the antimicrobial agent is present in the concentration range 2-400 parts per million.

19. A composition as claimed in claim 17 comprising grain, high protein materials, food by-products, vitamins, minerals or amino acids.

20. A premix composition for the preparation of a composition as claimed in claim 17 containing salbutamol or an acid addition salt thereof at a concentration in the range 0.01% to 2.0% by weight and an antimicrobial agent at a concentration in the range 1.0% to 10.0% by weight.

* * * * *